(12) United States Patent
Shefer et al.

(10) Patent No.: US 7,670,627 B2
(45) Date of Patent: Mar. 2, 2010

(54) PH TRIGGERED TARGETED CONTROLLED RELEASE SYSTEMS FOR THE DELIVERY OF PHARMACEUTICAL ACTIVE INGREDIENTS

(75) Inventors: Adi Shefer, Dayton, NJ (US); Samuel David Shefer, Dayton, NJ (US)

(73) Assignee: Salvona IP LLC, Dayton, NJ (US)

( * ) Notice: Subject to any disclaimer, the term of this patent is extended or adjusted under 35 U.S.C. 154(b) by 570 days.

(21) Appl. No.: 10/315,801

(22) Filed: Dec. 9, 2002

(65) Prior Publication Data

US 2004/0109894 A1 Jun. 10, 2004

(51) Int. Cl.
*A61K 9/14* (2006.01)
(52) U.S. Cl. .................. 424/502; 424/489; 424/493; 424/494; 424/495; 424/496; 424/497; 424/498; 424/499; 424/500; 424/501; 424/400
(58) Field of Classification Search .................. None
See application file for complete search history.

(56) References Cited

U.S. PATENT DOCUMENTS

| | | | |
|---|---|---|---|
| 3,686,025 A | 8/1972 | Morton | |
| 3,689,435 A | 9/1972 | Berni et al. | |
| 4,096,238 A | 6/1978 | Zaffaroni et al. | |
| 4,145,184 A | 3/1979 | Brain et al. | |
| 4,152,272 A | 5/1979 | Young | |
| 4,209,417 A | 6/1980 | Whyte | |
| 4,250,043 A | 2/1981 | Jones | |
| 4,402,856 A | 9/1983 | Schnoring et al. | |
| 4,434,086 A | 2/1984 | Hill et al. | |
| 4,446,032 A | 5/1984 | Munteanu et al. | |
| 4,464,271 A | 8/1984 | Munteanu et al. | |
| 4,476,041 A | 10/1984 | Hill et al. | |
| 4,488,973 A | 12/1984 | Hill et al. | |
| 4,503,030 A | 3/1985 | Edgren et al. | |
| 4,517,359 A | 5/1985 | Kobrehel et al. | |
| 4,520,009 A * | 5/1985 | Dunn .................. | 514/161 |
| 4,536,315 A | 8/1985 | Ramachandran et al. | |
| 4,578,075 A | 3/1986 | Urquhart et al. | |
| 4,587,117 A | 5/1986 | Edgren et al. | |
| 4,618,583 A | 10/1986 | Robison et al. | |
| 4,636,330 A | 1/1987 | Melville | |
| 4,681,583 A | 7/1987 | Urquhart et al. | |
| 4,689,223 A * | 8/1987 | Arias .................. | 424/682 |

(Continued)

FOREIGN PATENT DOCUMENTS

AU    B-54912/90    11/1990

(Continued)

*Primary Examiner*—Eric E. Silverman
(74) *Attorney, Agent, or Firm*—Porzio, Bromberg & Newman, P.C.

(57) ABSTRACT

The present invention relates to a novel pH triggered, targeted controlled release system. The controlled delivery system of the present invention is substantially a free-flowing powder formed of solid hydrophobic nano-spheres comprising pharmaceutical active ingredients that are encapsulated in a pH sensitive micro-spheres. The invention also relates to the processes for preparing the compositions and processes for using same. The controlled release system can be used to target and control the release of pharmaceutical active ingredients onto certain regions of the gastrointestinal tract including the stomach and the small intestine. The invention further pertains to pharmaceutical products comprising the controlled release system of the present invention.

58 Claims, 2 Drawing Sheets

Solid hydrophobic nano-spheres encapsulated in a pH sensitive micro-sphere

Solid hydrophobic nano-spheres

U.S. PATENT DOCUMENTS

| | | | |
|---|---|---|---|
| 4,842,761 A | 6/1989 | Rutherford | |
| 4,849,210 A * | 7/1989 | Widder | 424/9.322 |
| 4,851,231 A | 7/1989 | Urquhart et al. | |
| 4,910,021 A | 3/1990 | Davis et al. | |
| 4,919,841 A | 4/1990 | Kamel et al. | |
| 4,946,624 A | 8/1990 | Michael | |
| 4,954,285 A | 9/1990 | Wierenga et al. | |
| 5,066,419 A | 11/1991 | Walley et al. | |
| 5,094,761 A | 3/1992 | Trinh et al. | |
| 5,102,564 A | 4/1992 | Gardlik et al. | |
| 5,112,688 A | 5/1992 | Michael | |
| 5,137,646 A | 8/1992 | Schmidt et al. | |
| 5,154,842 A | 10/1992 | Walley et al. | |
| 5,175,003 A | 12/1992 | Goldman | |
| 5,188,753 A | 2/1993 | Schmidt et al. | |
| 5,207,933 A | 5/1993 | Trinh et al. | |
| 5,232,612 A | 8/1993 | Trinh et al. | |
| 5,232,613 A | 8/1993 | Bacon et al. | |
| 5,234,610 A | 8/1993 | Gardlik et al. | |
| 5,234,611 A | 8/1993 | Trinh et al. | |
| 5,236,615 A | 8/1993 | Trinh et al. | |
| 5,246,603 A | 9/1993 | Tsaur et al. | |
| 5,281,355 A | 1/1994 | Tsaur et al. | |
| 5,288,423 A | 2/1994 | Behan et al. | |
| 5,316,774 A | 5/1994 | Eury et al. | |
| 5,324,444 A | 6/1994 | Berry et al. | |
| 5,358,502 A | 10/1994 | Herbig et al. | |
| 5,385,959 A | 1/1995 | Tsaur et al. | |
| 5,425,887 A | 6/1995 | Lam et al. | |
| 5,484,610 A | 1/1996 | Bae | |
| 5,508,259 A | 4/1996 | Holzner et al. | |
| 5,543,158 A * | 8/1996 | Gref et al. | 424/501 |
| 5,554,147 A | 9/1996 | Batich et al. | |
| 5,562,847 A | 10/1996 | Waite et al. | |
| 5,609,590 A | 3/1997 | Herbig et al. | |
| 5,656,292 A | 8/1997 | Urtti et al. | |
| 5,656,584 A | 8/1997 | Angell et al. | |
| 5,668,097 A | 9/1997 | Trinh et al. | |
| 5,691,303 A | 11/1997 | Pan et al. | |
| 5,718,919 A * | 2/1998 | Ruddy et al. | 424/489 |
| 5,788,687 A | 8/1998 | Batich et al. | |
| 5,814,592 A | 9/1998 | Kahn et al. | |
| 5,840,668 A | 11/1998 | Behan et al. | |
| 5,858,959 A | 1/1999 | Surutzidis et al. | |
| 5,955,419 A | 9/1999 | Barket, Jr. et al. | |
| 6,024,943 A | 2/2000 | Ness et al. | |
| 6,025,319 A | 2/2000 | Surutzidis et al. | |
| 6,042,792 A | 3/2000 | Shefer et al. | |
| 6,048,830 A | 4/2000 | Gallon et al. | |
| 6,051,540 A | 4/2000 | Shefer et al. | |
| 6,068,859 A | 5/2000 | Curatolo et al. | |
| 6,093,691 A | 7/2000 | Sivik et al. | |
| 6,103,865 A | 8/2000 | Bae et al. | |
| 6,248,363 B1 * | 6/2001 | Patel et al. | 424/497 |
| 6,306,422 B1 | 10/2001 | Batich et al. | |
| 6,365,187 B2 | 4/2002 | Mathiowitz et al. | |
| 6,582,720 B1 * | 6/2003 | Inagi et al. | 424/434 |
| 6,589,562 B1 | 7/2003 | Shefer et al. | 424/490 |
| 6,602,524 B2 | 8/2003 | Batich et al. | 424/489 |

FOREIGN PATENT DOCUMENTS

| | | |
|---|---|---|
| EP | 0 334 490 | 9/1989 |
| EP | 0 334 490 B1 | 9/1989 |
| EP | 0 376 385 | 7/1990 |
| EP | 0 539 025 A2 | 4/1993 |
| EP | 0 469 228 B1 | 5/1996 |
| EP | 0 764 717 A1 | 3/1997 |
| EP | 0 908 174 A2 | 4/1999 |
| EP | 0 925 776 A2 | 6/1999 |
| WO | WO 93/05136 | 3/1993 |
| WO | WO 93/05137 | 3/1993 |
| WO | WO 93/05139 | 3/1993 |
| WO | WO 93/05141 | 3/1993 |
| WO | WO 93/13195 | 7/1993 |
| WO | WO 94/19448 | 9/1994 |
| WO | WO 94/27107 | 12/1994 |
| WO | WO 97/11152 | 3/1997 |
| WO | WO 97/34981 | 9/1997 |
| WO | WO 97/47720 | 12/1997 |
| WO | WO 98/12298 | 3/1998 |

* cited by examiner

PH TRIGGERED TARGETED CONTROLLED RELEASE SYSTEMS FOR THE DELIVERY OF PHARMACEUTICAL ACTIVE INGREDIENTS

BACKGROUND OF THE INVENTION

1. Field of the Invention

The present invention relates to a controlled drug delivery system comprising solid hydrophobic nano-spheres encapsulated in a pH sensitive micro-sphere for site-specific targeted controlled release of pharmaceutical active ingredients onto certain regions of the gastrointestinal (G-I) tract including the stomach and the small intestine to enhance their bioavailability and release of effective levels of drug in these regions over an extended period of time.

2. Description of the Related Art

Targeted drug delivery is a goal of the pharmaceutical industry. In targeted drug delivery the aim is to optimize drug efficacy by localizing its therapeutic effect to the site or organ of action. If successful, the targeting provides a significant reduction in drug toxicity, reduction of the drug dose, and increased treatment efficacy.

The oral route can be used for administering drugs that are absorbed into systemic circulation from all regions of the gastrointestinal tract including the stomach, small intestine and the large intestine, as well as for administering drugs that are absorbed into systemic circulation from certain regions of the gastrointestinal tract, mainly the stomach and the small intestine. Orally administered drugs must overcome several obstacles to reach their desired targets. The pH and enzymatic activities found in gastrointestinal fluids may inactivate the drug or cause the drug to dissolve poorly. In addition, following their absorption in the intestine, orally administered drugs are often subject to a "first pass" clearance by the liver and excreted into bile or converted into pharmacologically inactive metabolites. Decreased bioavailability of orally administered drugs is a consequence of this first pass effect. Also, the duration of orally administrated drugs is limited by the gastrointestinal retention time and drug efficacy depends upon the ability of the drug to reach its target in sufficient quantity to maintain therapeutic levels for the desired time period.

Extensive work has been directed in recent years towards creating delivery systems to target certain regions of the gastrointestinal tract including the stomach and the small intestine, mainly through coating technology, especially using pH sensitive polymers. These coatings have been modified to achieve longer time lags prior to release so that the beneficial agent can be released in the lower end of the small intestine or in the colon. However, these coatings were observed to function similarly as conventional enteric coatings.

Typically pH-sensitive materials have been used as coatings to protect beneficial agents, or to encapsulate irritating beneficial agents during transit through the stomach, and then release the agent shortly after entering the small intestine. pH-sensitive coatings that achieve delivery in the colon have been described in patents such as U.S. Pat. No. 4,910,021 and WO 9001329. U.S. Pat. No. 4,910,021 describes using a pH-sensitive material to coat a capsule. WO 9001329 describes using pH-sensitive coatings on beads containing acid, where the acid in the bead core prolongs dissolution of the pH-sensitive coating.

U.S. Pat. No. 6,068,859 discloses a controlled-release dosage form of azithromycin having an improved side effect profile; a process for preparing the dosage form; and a method of treating a microbial infection, comprising administering azithromycin in such a controlled-release dosage form to a mammal, including a human patient, in need of such treatment. A first delayed release embodiment according to the invention is a pH-dependent coated tablet which comprises a tablet core comprising azithromycin, a disintegrant, a lubricant, and one or more pharmaceutical carriers, such core being coated with a material, preferably a polymer, which is substantially insoluble and impermeable at the pH of the stomach, and which is more soluble and permeable at the pH of the small intestine. Preferably, the coating polymer is substantially insoluble and impermeable at pH<5.0, and water-soluble at pH>5.0.

U.S. Pat. No. 5,175,003 discloses a dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with a drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher.

U.S. Pat. No. 4,503,030 discloses an osmotic device for dispensing a drug to certain pH regions of the gastrointestinal tract. More particularly, the invention relates to an osmotic device comprising a wall formed of a semi-permeable pH sensitive composition that surrounds a compartment containing a drug, with a passageway through the wall connecting the exterior of the device with the compartment. The device delivers the drug at a controlled rate in the region of the gastrointestinal tract having a pH of less than 3.5, and the device self-destructs and releases all its drug in the region of the gastrointestinal tract having a pH greater than 3.5, thereby providing total availability for drug absorption.

U.S. Pat. Nos. 5,609,590 and 5,358,502 disclose an osmotic bursting device for dispensing a beneficial agent to an aqueous environment. The device comprises a beneficial agent and osmagent surrounded at least in part by a semi-permeable membrane. Alternatively the beneficial agent may also function as the osmagent. The semi-permeable membrane is permeable to water and substantially impermeable to the beneficial agent and osmagent. A trigger means is attached to the semi-permeable membrane (e.g., joins two capsule halves). The trigger means is activated by a pH of from 3 to 9 and triggers the eventual, but sudden, delivery of the beneficial agent. These devices enable the pH-triggered release of the beneficial agent core as a bolus by osmotic bursting.

U.S. Pat. No. 5,316,774 discloses a composition for the controlled release of an active substance comprising a polymeric particle matrix, where each particle defines a network of internal pores. The active substance is entrapped within the pore network together with a blocking agent having physical and chemical characteristics selected to modify the release rate of the active substance from the internal pore network. In an exemplary embodiment, drugs may be selectively delivered to the intestines using an enteric material as the blocking agent. The enteric material remains intact in the stomach but degrades under the pH conditions of the intestines. In another exemplary embodiment, the sustained release formulation employs a blocking agent, which remains stable under the expected conditions of the environment to which the active substance is to be released. The use of pH-sensitive materials alone to achieve site-specific delivery is difficult because of leaking of the beneficial agent prior to the release site or desired delivery time and it is difficult to achieve long time lags before release of the active ingredient after exposure to high pH (because of rapid dissolution or degradation of the pH-sensitive materials).

There are also hybrid systems which combine pH-sensitive materials and osmotic delivery systems. These devices provide delayed initiation of sustained-release of the beneficial agent. In one device a pH-sensitive matrix or coating dissolves releasing osmotic devices that provide sustained release of the beneficial agent see U.S. Pat. Nos. 4,578,075, 4,681,583, and 4,851,231. A second device consists of a semipermeable coating made of a polymer blend of an insoluble and a pH-sensitive material. As the pH increases, the permeability of the coating increases, increasing the rate of release of beneficial agent see U.S. Pat. Nos. 4,096,238, 4,503,030, 4,522,625, and 4,587,117.

U.S. Pat. No. 5,484,610 discloses terpolymers which are sensitive to pH and temperature which are useful carriers for conducting bioactive agents through the gastric juices of the stomach in a protected form. The terpolymers swell at the higher physiologic pH of the intestinal tract causing release of the bioactive agents into the intestine. The terpolymers are linear and are made up of 35 to 99 wt % of a temperature sensitive component, which imparts to the terpolymer LCST (lower critical solution temperature) properties below body temperatures, 1 to 30 wt % of a pH sensitive component having a $pK_a$ in the range of from 2 to 8 which functions through ionization or deionization of carboxylic acid groups to prevent the bioactive agent from being lost at low pH but allows bioactive agent release at physiological pH of about 7.4 and a hydrophobic component which stabilizes the LCST below body temperatures and compensates for bioactive agent effects on the terpolymers. The terpolymers provide for safe bioactive agent loading, a simple procedure for dosage form fabrication and the terpolymer functions as a protective carrier in the acidic environment of the stomach and also protects the bioactive agents from digestive enzymes until the bioactive agent is released in the intestinal tract.

U.S. Pat. No. 6,103,865 discloses pH-sensitive polymers containing sulfonamide groups, which can be changed in physical properties, such as swellability and solubility, depending on pH and which can be applied for a drug-delivery system, bio-material, sensor, and the like, and a preparation method therefore. The pH-sensitive polymers are prepared by introduction of sulfonamide groups, various in pKa, to hydrophilic groups of polymers either through coupling to the hydrophilic groups of polymers, such as acrylamide, N,N-dimethylacrylamide, acrylic acid, N-isopropylacrylamide and the like or copolymerization with other polymerizable monomers. These pH-sensitive polymers may have a structure of linear polymer, grafted copolymer, hydrogel or interpenetrating network polymer.

U.S. Pat. No. 5,656,292 discloses a composition for pH dependent or pH regulated controlled release of active ingredients especially drugs. The composition consists of a compactable mixture of the active ingredient and starch molecules substituted with acetate and dicarboxylate residues. The preferred dicarboxylate acid is succinate. The average substitution degree of the acetate residue is at least 1 and 0.2-1.2 for the dicarboxylate residue. The starch molecules can have the acetate and dicarboxylate residues attached to the same starch molecule backbone or attached to separate starch molecule backbones. The present invention also discloses methods for preparing said starch acetate dicarboxylates by transesterification or mixing of starch acetates and starch dicarboxylates respectively.

U.S. Pat. Nos. 5,554,147, 5,788,687, and 6,306,422 disclose a method for the controlled release of a biologically active agent wherein the agent is released from a hydrophobic, pH-sensitive polymer matrix. The polymer matrix swells when the environment reaches pH 8.5, releasing the active agent. A polymer of hydrophobic and weakly acidic comonomers is disclosed for use in the controlled release system. Also disclosed is a specific embodiment in which the controlled release system may be used. The pH-sensitive polymer is coated onto a latex catheter used in ureteral catheterization. A ureteral catheter coated with a pH-sensitive polymer having an antibiotic or urease inhibitor trapped within its matrix will release the active agent when exposed to high pH urine.

Mathiowitz et al U.S. Pat. No. 6,365,187 discloses Bioadhesive polymers in the form of, or as a coating on, microcapsules containing drugs or bioactive substances which may serve for therapeutic, or diagnostic purposes in diseases of the gastrointestinal tract, are described. The polymeric microspheres all have a bioadhesive force of at least 11 mN/cm-.sup.2 (110 N/m$^2$) Techniques for the fabrication of bioadhesive microspheres, as well as a method for measuring bioadhesive forces between microspheres and selected segments of the gastrointestinal tract in vitro are also described. This quantitative method provides a means to establish a correlation between the chemical nature, the surface morphology and the dimensions of drug-loaded microspheres on one hand and bioadhesive forces on the other, allowing the screening of the most promising materials from a relatively large group of natural and synthetic polymers which, from theoretical consideration, should be used for making bioadhesive microspheres.

The present invention addresses the ongoing need for an oral drug delivery system for site-specific targeted controlled delivery of drug to certain regions of the gastrointestinal tract including the stomach and the small intestine to enhance bioavailability and maximize the amount of drug available for absorption in these regions over an extended period of time. The prior art of which applicant is aware does not set forth a targeted controlled delivery system that is activated by pH to enhance deposition and extend the release of active ingredients onto certain regions of the gastrointestinal tract including the stomach and the small intestine over an extended period of time.

Azithromycin is the U.S.A.N. (generic name) for 9a-aza-9a-methyl-9-deoxo-9a-homoerythromycin A, a broad spectrum antimicrobial compound derived from erythromycin A and is being used for treating a microbial infection. Azithromycin is described in U.S. Pat. No. 4,474,768 and Kobrehel et al., U.S. Pat. No. 4,517,359, as is shown in FIG. 1. These patents disclose that azithromycin and certain derivatives thereof possess antimicrobial properties and are accordingly useful as antibiotics. Encapsulated Azithromycin in dosage form is disclosed in U.S. Pat. No. 6,068,859.

It is widely known that oral dosing of azithromycin can result in the occurrence, in some patients, of adverse gastrointestinal (GI) side effects, such as cramping, diarrhea, nausea, and vomiting. The incidence of gastrointestinal side effects is higher at higher doses than at lower doses.

Dosing azithromycin orally in conventional non-controlled-release capsules results in relatively extensive exposure of drug to the duodenum. Dosing of azithromycin in conventional enteric dosage forms which prevent significant dissolution of the drug in the stomach can also expose the duodenum to a large proportion of the azithromycin dose.

SUMMARY OF THE INVENTION

The present invention relates to an improved carrier system for site-specific targeted controlled delivery of pharmaceutical active ingredients onto certain regions of the gastrointestinal tract including the stomach and the small intestine to enhance their bioavailability and release effective levels of the pharmaceutically active ingredients in these regions over an extended period of time. More particularly, the invention relates to a controlled release system comprising solid hydrophobic nano-spheres encapsulated in a pH sensitive microsphere. The surface properties of the nano-spheres can be modified to enhance the affinity of the nano-spheres for a specific site, a particular residue expressed on a cell surface, or enhance their affinity for a cell surface protein or receptor. Pharmaceutical active ingredients can be incorporated in the hydrophobic nano-spheres, in the pH sensitive microspheres, or in both the nano and micro-spheres.

The active ingredients and the nano-spheres are released from the micro-sphere when the pH of the surrounding environment reaches a desired level. This method of controlled release ensures that the nano-spheres comprising the active ingredients are delivered to a specific site and delivered only where the need for the active agent arises. Upon changes in pH, the micro-sphere pH sensitive matrix materials dissolve or swell. The dissolution or swelling of the matrix disrupts the micro-sphere structure and facilitates the release of the nano-spheres and the active ingredients. The deposition of the nano-spheres onto the target surface is improved by optimizing particle size to ensure entrainment of the nano-spheres within target surface and by modifying their surface to enhance the affinity of the nano-spheres for a particular residue expressed on a cell surface or enhance their affinity for a cell surface protein or receptor to maximize interaction between the nano-spheres and the target surface.

Various chemical groups and bioadhesive materials can be incorporated in the nano-spheres structure to improve the interaction between the nano-spheres and the target surface, depending on the target surface. A cationic surface active agent creates positively charged nano-spheres; an anionic surface active agent creates negatively charged nano-spheres; a nonionic surface active creates neutral charged nano-spheres; and a zwitterionic surface active agent creates variable charged nano-spheres.

In one embodiment, the nano-spheres of the present invention are bioadhesive. Bioadhesive nano-sphere can be created by incorporating a bioadhesive material into the solid hydrophobic matrix of the nano-spheres, by incorporating a bioadhesive material in the pH sensitive micro-sphere matrix, or by using a bioadhesive material in the nano-sphere matrix in conjunction with bioadhesive material in the micro-sphere matrix.

The nano-spheres of the present invention can also comprise ligands that minimize tissue adhesion or that target the nano-spheres to specific cell or tissue with a high degree of selectivity. The controlled delivery system of the present invention is useful for oral delivery of pharmaceutical active ingredients and to enhance diagnostic imaging.

The carrier system of the present invention is a free-flowing powder formed of solid hydrophobic nano-spheres comprising various active ingredients, that are encapsulated in a pH sensitive micro-spheres, having the advantages of:

(i) protection of the pharmaceutical active ingredients, during storage, or until needed and reaches the target site;

(ii) pH triggered release of a first pharmaceutical active ingredient from the microspheres and of a second pharmaceutical active ingredient from the nano-spheres in response to change in pH in the system proximate environment, and, (iii) site specific targeted delivery and enhanced deposition of the nano-spheres comprising pharmaceutical active ingredients, onto the target surface;

(iv) enhanced bioavailability of pharmaceutical active ingredients encapsulated in the nano-spheres; and (v) prolonged release of pharmaceutical active ingredients encapsulated in the nano-spheres, over an extended period of time.

The invention also provides a method for producing the multi component controlled release system of the present invention including active ingredients that comprises the steps of:

(i) incorporating the pharmaceutical active ingredients into solid hydrophobic nano-spheres;

(ii) forming an aqueous mixture comprising of one or more pharmaceutical active agents, the nano-spheres, and pH sensitive materials; and (iii) spray drying the mixture to form a dry powder composition.

The invention further provides a process for producing the multi component controlled release system of the present invention including the pharmaceutical active ingredients that comprises the steps of:

(i) heating hydrophobic materials to a temperature above the melting point of the materials to form a melt;

(ii) dissolving or dispersing a first pharmaceutical active agent into the melt;

(iii) dissolving or dispersing a second pharmaceutical active agent, pH sensitive material, and a targeting material, in the aqueous phase;

(iv) heating the composition to above the melting temperature of the hydrophobic materials;

(v) mixing the hot melt with the aqueous phase to form a dispersion;

(vi) high shear homogenization of the dispersion at a temperature above the melting temperature until a homogeneous fine dispersion is obtained having a sphere size of from about 1 micron to about 2 microns;

(vii) cooling the dispersion to ambient temperature; and (viii) spray drying the emulsified mixed suspension to form a dry powder composition.

The invention also provides pharmaceutical products comprising the multi component controlled release system of the present invention.

The invention will be more fully described by reference to the following drawings:

DETAILED DESCRIPTION

Figure 1:
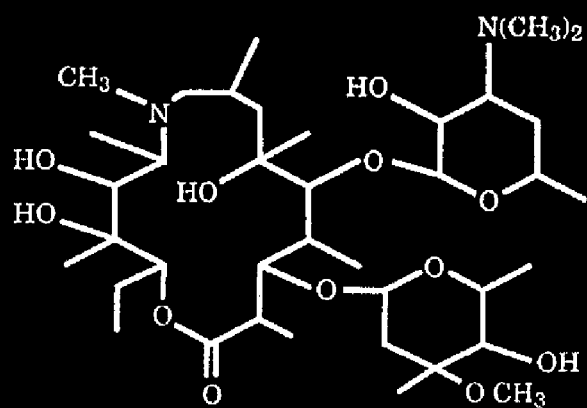
FIG. 1 is a schematic diagram of azithromycin.
Figure 2:
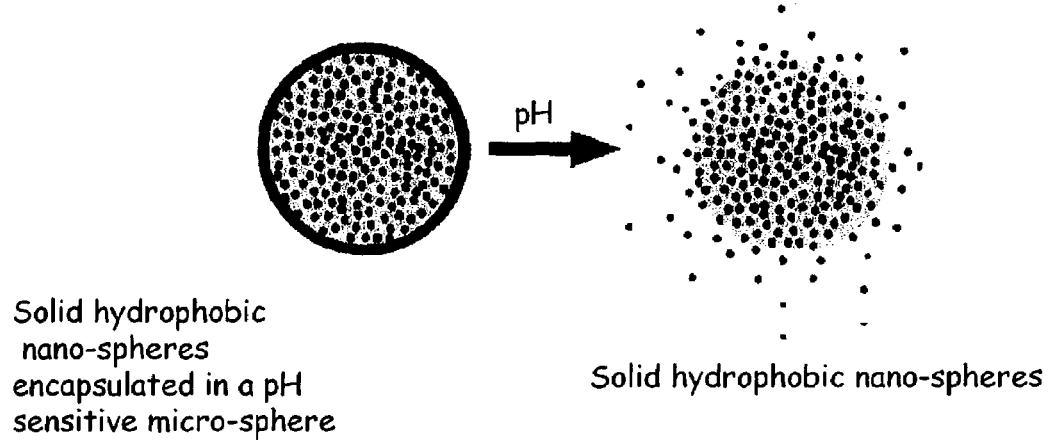
FIG. 2 is a schematic diagram of a controlled release system of the present invention.

The present invention provides a method of controlling the release rate of pharmaceutical active ingredients, that can be incorporated in pharmaceutical products, the present invention provides site specific targeted delivery, enhanced bioavailability, and sustained release of pharmaceutical active ingredients over an extended period of time. The delivery system of the present invention comprises a free-flowing, powder formed of solid hydrophobic nano-spheres comprising pharmaceutical active ingredients, that are encapsulated in a pH sensitive micro-sphere, as shown in FIG. 2. The composition is activated by changes in pH in the system proximate environment, to provide targeted delivery, enhanced bioavailability, and prolonged release of pharmaceutical active ingredients over an extended period of time. The surface properties of the nano-spheres can be modified to enhance the affinity of the nano-spheres for a particular residue expressed on a cell surface or the affinity of the nano-spheres for a cell surface protein or receptor. Pharmaceutical active ingredients can be incorporated in the hydrophobic nano-spheres, in the pH sensitive micro-spheres, or in both the nano and micro-spheres. A first pharmaceutical active ingredient can be incorporated in the nano-sphere and a second pharmaceutical active ingredient which is different from the first pharmaceutical active ingredient can be incorporated into the micro-sphere.

The term "spheres" is intended to describe solid, substantially spherical particulates. It will be appreciated that the term "sphere" includes other particle shapes that can be formed in accordance with the teachings of the present invention.

The term "pH triggered release" is intended to mean that the rate of release is dependent of or regulated by the pH of the system surrounding media or environment.

The active ingredients and the nano-spheres are released from the micro-sphere when the pH of the surrounding environment reaches a desired level. The controlled release method of the present invention ensures that the nano-spheres comprising the active ingredients are delivered to a specific site in the G-I tract and are delivered to where the need for the active agent arises. Upon changes in pH, pH sensitive matrix materials of the micro-sphere dissolve or swell. The dissolution or swelling of the matrix disrupts the micro-sphere structure and facilitates the release of the nano-spheres and the active ingredients contained in the microspheres. The deposition of the nano-spheres onto the target surface is improved by optimizing particle size to ensure entrainment of the nano-spheres within a target surface and by modifying their surface to enhance the affinity of the nano-spheres for a particular residue expressed on a cell surface or their affinity for a cell surface protein or receptor to maximize interaction between the particles and the target surface.

With respect to the interaction between the nano-spheres and the target surface, various chemical groups and bioadhesive materials can be incorporated in the nano-spheres structure, for improving interaction with the target surface. A cationic surface active agent creates positively charged nano-spheres; an anionic surface active agent creates negatively charged nano-spheres; a nonionic surface active creates neutral charged nano-spheres; and a zwitterionic surface active agent creates variable charged nano-spheres.

In one embodiment, the nano-spheres of the present invention are bioadhesive. Bioadhesive nano-sphere can be created by incorporating a bioadhesive material into the solid hydrophobic matrix of the nano-spheres, by incorporating a bioadhesive material in the pH sensitive micro-sphere matrix, or by using a bioadhesive material in the nano-sphere matrix in conjunction with bioadhesive material in the micro-sphere matrix.

The multi-component controlled release system of the present invention can comprise from about 1% to about 50% by weight hydrophobic matrix, from about 1% to about 50% by weight pH sensitive matrix, from about 0% to about 10% by weight targeting materials, from about 0% to about 20% by weight surface active agents, and from about 0.01% to about 50% by weight active ingredients. The hydrophobic matrix enhances bioavailability and sustains the diffusion rate of the pharmaceutical active ingredients, through the nano-spheres and enables them to be released onto the target site over an extended period of time. The micro-sphere has an average sphere size in the range from about 20 microns to about 100 microns. The nano-sphere has an average sphere size in the range from about 0.01 micron to about 5 microns and has a melting point in the range from about 30 degrees C. to about 90 degrees C. This linear dimension for any individual sphere represents the length of the longest straight line joining two points on the surface of the sphere.

Additional components can be added to the carrier system or can be incorporated into the nano-spheres, the micro-spheres, or both the nano and micro spheres matrices. The controlled release system of the present invention can readily include other pharmaceutical active agents, including, but are not limited to: anti-oxidants; free radical scavengers; anti-microbial agents; antibacterial agents; allergy inhibitors; anti-aging agents; antiseptics; analgesics; anti-hair loss agents; hair growth promoting agents; hair growth inhibitor agents; keratolytic agents; anti-inflammatory agents; healing agents; anti invectives; inflammation inhibitors; vasoconstrictors; vasodilators; wound healing promoters; peptides, polypeptides and proteins; anti-fungal; depilating agents; counterirritants; vitamins; amino acids and their derivatives; herbal extracts; flavoids; chelating agents; cell turnover enhancers; and nourishing agents. The additional components are usually present in an amount from about 1% to about 20% by weight of the spheres.

The controlled release system of the present invention can readily include additional pharmaceutical active agents. The additional components are usually present in an amount from about 1% to about 20% by weight of the spheres.

The controlled release compositions of the present invention can be easily processed into articles of predetermined generic dimensions. Examples of articles include pharmaceutical, diagnostic, implant, imaging, and the like.

I. Matrix Materials for Forming the Nano-Spheres

Considerations in the selection of the matrix material include good barrier properties to the active ingredients, low toxicity and irritancy, stability, integrity, and high loading capacity for the active agents of interest. Suitable wax materials for the compositions and devices of the present invention are inert nontoxic materials with a melting point range between about 25 degrees C. and about 150 degrees C. and penetration point of about 1 to about 10. Examples of wax materials include natural waxes, synthetic waxes and mixtures thereof. Suitable waxes also include natural, regenerated, or synthetic food approved waxes including animal waxes such as beeswax, vegetable waxes such as carnauba, candelilla, sugar cane, rice bran, and bayberry wax, mineral waxes such as petroleum waxes including paraffin and micro-crystalline wax, and mixtures thereof.

Other wax materials that are known to those skilled in the art and suitable materials as described in "Industrial Waxes" Vol. I and II, by Bennett F.A.I.C., published by Chemical Publishing Company Inc., 1975 and Martindale, "The Extra Pharmacopoeia", The Pharmaceutical Press, $28^{th}$ Edition pp. 1063-1072, 1982 can be used in the present invention.

Suitable fat materials and/or glyceride materials which can be used as matrix materials for forming the nano-spheres of the present invention include, but are not limited to, the following classes of lipids: mono-, di and triglycerides, phospholipids, sphingolipids, cholesterol and steroid derivatives, terpenes and vitamins.

The fat material of the present invention can be a glyceride selected from monoglycerides, diglycerides, glyceryl monostearate, glyceryl tristearate and mixtures thereof. Other fat materials which can be used are hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil, partially hydrogenated soybean oil, partially hydrogenated cottonseed oil, and mixtures thereof.

Examples of solid fat materials which can be used in the present invention, include solid hydrogenated castor and vegetable oils, hard fats, and mixtures thereof. Other fat materials which can be used, include triglycerides of food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10-C18), denoted medium chain triglycerides (MCT). The fatty acid moieties of such triglycerides can be unsaturated or polyunsaturated and mixtures of triglycerides having various fatty acid material.

Phospholipids which can be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and beta-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) can also be used.

Steroids which can be used include as fat materials, but are not limited to, cholesterol, cholesterol sulfate, cholesterol hemisuccinate, 6-(5-cholesterol 3 beta-yloxy) hexyl6-amino-6-deoxy-1-thio-alpha-D-galactopyranoside, 6-(5-cholesten-3 beta-loxy)hexyl-6-amino-6-deoxyl-1-thio-alpha-D mannopyranoside and cholesteryl)4'-trimethyl 35 ammonio) butanoate.

Additional lipid compounds as fat material which can be used include tocopherol and derivatives, and oils and derivatized oils such as stearylamine.

The fat material can be fatty acids and derivatives thereof which can include, but are not limited to, saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that can be used include, but are not limited to, molecules that have between 12 carbon atoms and 22 carbon atoms in either linear or branched form. Examples of saturated fatty acids that can be used include, but are not limited to, lauric, myristic, palmitic, and stearic acids. Examples of unsaturated fatty acids that can be used include, but are not limited to, lauric, physeteric, myristoleic, palmitoleic, petroselinic, and oleic acids. Examples of branched fatty acids that can be used include, but are not limited to, isolauric, isomyristic, isopalmitic, and isostearic acids and isoprenoids. Fatty acid derivatives include 12-(((7'-diethylaminocoumarin-3-yl)carbonyl)methylamino)-octadecanoic acid; N-[12-(((7'diethylaminocoumarin-3-yl)carbonyl)methyl-amino)octadecanoyl]-2-aminopalmitic acid, N succinyl-dioleoylphosphatidylethanol amine and palmitoyl-homocysteine; and/or combinations thereof. Mono, di and triglycerides or derivatives thereof that can be used include, but are not limited to, molecules that have fatty acids or mixtures of fatty acids between 6 and 24 carbon atoms, digalactosyldiglyceride, 1,2-dioleoyl-sn-glycerol; 1,2-cdipalmitoyl-sn-3 succinylglycerol; and 1,3-dipalmitoyl-2-succinylglycerol.

The nano-spheres of the present invention can have a melting point in the range from about 30 degrees C. to about 90 degrees C., preferably from about 40 degrees C. to about 90 degrees C. The melting point of the spheres is typically a function of the carrier matrix employed. Accordingly, preferred matrix materials have a melting point in the range of about 50 degrees C. to about 80 degrees C., preferably from about 60 degrees C. to about 70 degrees C. It should be understood that it is the melting point of the sphere rather than the melting point of the carrier matrix that is important for use of the carrier system of the present invention.

II. Materials for Forming a Micro-Sphere Matrix

The micro-sphere can be composed of purely pH sensitive materials or comprise of a mixture of pH sensitive materials and water sensitive or bioadhesive materials.

pH and Salt Sensitive Materials

Any material and structural form may be used as the pH-sensitive or salt-sensitive trigger means that maintains the integrity of the micro-sphere until triggered by a solution of the desired pH. Typically, the trigger pH is between about 3 to 12, although in some applications it may be higher or lower. The trigger pH is the threshold pH value or range of values at which either above or below the trigger pH the pH-sensitive material degrades, and/or dissolves. The micro-sphere can be formed to be stable in solutions and then as the pH rises above the trigger pH the micro-spheres are activated. Likewise, micro-spheres can be formed to be stable in solutions and as the pH drops below the trigger pH the micro-spheres are activated. Once activated, the active ingredients and the nano-spheres are released.

In one embodiment a pH-sensitive trigger means is used that the micro-sphere is capable of becoming more permeable to water and/or losing physical strength following triggering by a solution of the desired pH, either above or below the trigger pH, or salt concentration. In another embodiment a pH-sensitive trigger means is used to hold together two nano-sphere portions. The trigger means is capable of losing its adhesive quality or strength, such as to degrade or dissolve, following triggering by a solution of the desired pH, either above or below the trigger pH, or following a change in salt concentration. The reduction in adhesion strength allows the hydrostatic pressure inside the micro-sphere core to push apart the nano-spheres portions held together by the adhesive trigger means, thus releasing the contents.

The pH-sensitive materials can be insoluble solids in acidic or basic aqueous solutions, which dissolve, or degrade and dissolve, as the pH of the solution is neutral. The pH-sensitive materials can be insoluble solids in acidic or basic aqueous solutions which dissolve, or degrade and dissolve, as the pH of the solution rises above or drops below a trigger pH value.

Exemplary pH-sensitive materials include copolymers of acrylate polymers with amino substituents, acrylic acid esters, polyacrylamides, phthalate derivatives (i.e., compounds with covalently attached phthalate moieties) such as acid phthalates of carbohydrates, amylose acetate phthalate, cellulose acetate phthalate, other cellulose ester phthalates, cellulose ether phthalates, hydroxypropyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers.

Examples of suitable pH sensitive polymers for use are the Eudragit® polymers series from Rohm America Inc., a wholly-owned subsidiary of Degussa-Huls Corporation, headquartered in Piscataway, N.J., and an affiliate of Rohm GmbH of Darmstadt, Germany. EUDRAGIT® L 30 D-55 and EUDRAGIT® L 100-55, pH dependent anionic polymer that is soluble at pH above 5.5 and insoluble below pH 5. These polymers can be utilized for targeted drug delivery in the duodenum. EUDRAGIT® L 100 pH dependent anionic polymer that is soluble at pH above 6.0 for targeted drug delivery in the jejunum. EUDRAGIT® S 100 pH dependent anionic polymer that is soluble at pH above 7.0 for targeted drug delivery in the ileum. EUDRAGIT® E 100 and EUDRAGIT® EPO, pH dependent cationic polymer, soluble up to pH 5.0 and insoluble above pH 5.0. dependent cationic polymer, soluble up to pH 5.0 and insoluble above pH 5.0. Accordingly, suitable pH sensitive materials degrade or dissolve when said pH sensitive micro-sphere contacts a solution having a pH greater than about 5.

Additional pH-sensitive materials include poly functional polymers containing multiple groups that become ionized as the pH drops below their pKa. A sufficient quantity of these ionizable groups must be incorporated in the polymer such that in aqueous solutions having a pH below the pKa of the ionizable groups, the polymer dissolves. These ionizable groups can be incorporated into polymers as block copolymers, or can be pendent groups attached to a polymer backbone, or can be a portion of a material used to crosslink or connect polymer chains. Examples of such ionizable groups include polyphosphene, vinyl pyridine, vinyl aniline, polylysine, polyornithine, other proteins, and polymers with substituents containing amino moieties.

pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Other pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

Anionic acrylic copolymers of methacrylic acid and methylmethacrylate are also particularly useful coating materials for delaying the release of compositions and devices until the compositions and devices have moved to a position in the small intestine which is distal to the duodenum. Copolymers of this type are available from RohmPharma Corp, under the trade names Eudragit-L.R™ and Eudragit-S.R™, are anionic copolymers of methacrylic acid and methylmethacrylate. The ratio of free carboxyl groups to the esters is approximately 1:1 in Eudragit-L.R™ and approximately 1:2 in Eudragit-S.R™. Mixtures of Eudragit-L.R™ and Eudragit-S.R™ can also be used.

Other pH-sensitive materials are cationic pH sensitive polymers and copolymers that are water insoluble at pH 9 and above and are water soluble or water dispersible at pH 7.

The pH-sensitive and salt sensitive materials can be blended with an inert water sensitive material. By inert is meant a material that is not substantially affected by a change in pH or salt concentration in the triggering range. By altering the proportion of a pH-sensitive material to inert material the time lag subsequent to triggering and prior to release can be tailored.

In an embodiment of the present invention, the micro sphere is formed of a pH sensitive material which is substantially insoluble and impermeable at the pH of the stomach, and is more soluble and permeable at the pH of the small intestine. Preferably, the micro spheres are substantially insoluble and impermeable at pH less than about 5.0, and water-soluble at pH greater than about 5.0. pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; vinyl acetate; crotonic acid copolymers and Eudragit® polymers series from Rohm America Inc.

Water Sensitive Materials

Water-sensitive materials can be mixed with the pH or salt sensitive materials to form the micro-spheres of the present invention. Suitable water sensitive materials comprise polyvinyl pyrrolidone, water soluble celluloses, polyvinyl alcohol, ethylene maleic anhydride copolymer, methyl vinyl ether maleic anhydride copolymer, polyethylene oxides, water soluble polyamide or polyester, copolymers or homopolymers of acrylic acid such as polyacrylic acid, polystyrene acrylic acid copolymers or starch derivatives, polyvinyl alcohol, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

The polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I-XIV of U.S. Pat. No. 5,051,222 issued on Sep. 24, 1991, the specification for which is incorporated by reference herein.

Polyvinyl alcohol useful for practice of the present invention is Mowiol® 3-83, having a molecular weight of about 14,000 Da and degree of hydrolysis of about 83%, Mowiol® 3-98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000-27,000 Da and degree of hydrolysis of about 88%, and VINEX® 1025, having molecular weight of 15,000-27,000 Da degree of hydrolysis of about 99% and commercially available from Air Products & Chemicals, Inc. of Allentown, Pa.; ELVANOL® 51-05, having a molecular weight of about 22,000-26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9-6, Nozaki Cho, Kita-Ku, Osaka, 530 Japan.

Suitable polysaccharides are polysaccharides of the non-sweet, colloidally soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

Bioadhesive Polymers

An orally ingested drug delivery system can adhere to either the epithelial surface or the mucus. For the delivery of bioactive active ingredients, it is advantageous to have the system adhere to the epithelium rather than solely to the mucous layer, although mucoadhesion can also substantially improve bioavailability. For some types of imaging purposes, adhesion to both the epithelium and mucus is desirable whereas in pathological states, such as in the case of gastric ulcers or ulcerative colitis, adhesion to cells below the mucous layer may occur. Duchene, et al., Drug Dev. Ind. Pharm. 14(2&3), 283-318 (1988), reviews the pharmaceutical and medical aspects of bioadhesive systems for drug delivery. "Bioadhesion" is defined as the ability of a material to adhere to a biological tissue for an extended period of time. Bioadhesion is a solution to the problem of inadequate residence time resulting from the stomach emptying and intestinal peristalsis, and from displacement by ciliary movement. For sufficient bioadhesion to occur, an intimate contact is needed between the bioadhesive and the receptor tissue, the bioadhesive must penetrate into the crevice of the tissue surface and/or mucus, and mechanical, electrostatic, or chemical bonds form. Bioadhesive properties of the polymers are affected by both the nature of the polymer and by the nature of the surrounding media.

Incorporating bioadhesive polymers in the micro-sphere of the present invention can be utilized to control or increase the absorption of the nano-sphere through the mucosal lining, or to further delay transit of the nano-sphere through the gastrointestinal passages.

A bioadhesive polymer as used in the disclosure is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues can be achieved by (i) physical or mechanical bonds, (ii) primary or covalent chemical bonds, and/or (iii) secondary chemical bonds such as ionic. Physical or mechanical bonds can result from deposition and inclusion of the bioadhesive material in the crevices of the mucus or the folds of the mucosa. Secondary chemical bonds, contributing to bioadhesive properties, can comprise dispersive interactions such as Van der Waals interactions and stronger specific interactions, such as hydrogen bonds. Hydrophilic functional groups primarily responsible for forming hydrogen bonds include hydroxyl and the carboxylic groups. Suitable bioadhesive polymers for use in the present invention include bio-erodible hydrogels as described by H. S. Sawhney, C. P. Pathak and J. A. Hubell in Macromolecules. 1993, 26:581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly (butyl methacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) and poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers can be combined with metal oxide particles to improve bioadhesion in addition to the use of organic additives alone. Organic dyes because of their electronic charge and hydrophobicity/hydrophilicity can either increase or decrease the bioadhesive properties of polymers when incorporated into the polymers. The incorporation of oligomer compounds into a wide range of different polymers which are not normally bioadhesive can be used to increase the adherence of the polymer to tissue surfaces such as mucosal membranes.

III. Targeting Mechanism

The nano-spheres can be targeted specifically or non-specifically through the selection of the pH of the material forming the micro-sphere, the size of the nano-sphere, and/or incorporation or attachment of a ligand to the nano-spheres. For example, biologically active molecules, or molecules affecting the charge, lipophilicity or hydrophilicity of the nano-spheres, can be attached to the surface of the nano-spheres. Additionally, molecules can be attached to the nano-spheres which minimize tissue adhesion, or which facilitate specific targeting of the nano-sphere in vivo. Representative targeting molecules include antibodies, lectins, and other molecules which are specifically bound by receptors on the surfaces of cells of a particular type.

In one embodiment of the present invention, the nano-spheres are modified with lectins attached to the nanosphere surface and targeted to mucosal epithelium of the small intestine and are absorbed into the systemic circulation and lymphatic circulation. In an embodiment of the present invention, carbohydrates or lectins are used to target the nano-spheres of the present invention to M cells and Peyer's Patch cells of the small intestine. In another embodiment of the present invention, lectins which bind to fucosyl sugars are used to modify the nano-spheres. Lectins are a heterogenous group of proteins or glycoproteins that recognize carbohydrate residues on cell surface glycoconjugates with a high degree of specificity. Examples of lectins that can be used to modify the nano-spheres of the present invention, include but are not limited to, lectins specific for binding to fucosyl glycoconjugates, such as Ulex Europeas Agglutinin I (UEA); lectins specific for binding to galactose/N-acetylgalactoseamine, such as *Phaseolus vulgaris* haemagglutinin (PHA), tomato lectin (*Lycopersicon esculentum*) (TL), wheat germ agglutinin (WGA); lectins specific for binding to mannose, such as, *Galanthus nivalis* agglutinin (GNA); lectins specific for mannose and/or glucose, such as, con A/concavalan A. (See e.g., Lehr et al., 1995, in Lectins Biomedical Perspectives, pp. 117-140, incorporated by reference into this application). The targeting molecules can be derivatized if desired. See e.g., Chen et al., 1995, Proceed. Internat. Symp. Control. Rel. Bioact. Mater. 22 and Cohen WO 9503035, incorporated by reference into this application.

In another embodiment of the invention, the nano-spheres of the present invention can be modified with viral proteins or bacterial proteins that have an affinity for a particular residue expressed on a cell surface or that have an affinity for a cell surface protein or receptor. Examples of such proteins include, but are not limited to, cholera toxin B subunit, and bacterial adhesotopes.

In yet another embodiment of the present invention, the nano-spheres of the present invention can be modified with monoclonal antibodies or fragments of antibodies which target the nano-spheres to a particular cell type. The nano-spheres of the present invention can be modified with ligands for specific mucosal cell surface receptors and proteins. As used herein, the term "ligand" refers to a ligand attached to a nano-sphere which adheres to the mucosa in the intestine or can be used to target the nano-spheres to a specific cell type in the G-I tract or following absorption of the nanospheres onto the mucosa in the intestine. Suitable ligands can include ligands for specific cell surface proteins and antibodies or antibody fragments immunoreactive with specific surface molecules. Suitable ligands can also include less specific targeting ligands such as coatings of materials which are bioadhesive, for example alginate and polyacrylate.

IV. Active Ingredients

Pharmaceutical active agents which can be used in the present invention can be selected from analgesics, anti-inflammatory agents, anthelmintics, anti-arrhythmic agents, anti-bacterial agents, anti-viral agents, anti-coagulants, antidepressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, beta-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents anti-obesity agents, cognition enhancers, anti-urinary incontinence agents, nutritional oils, anti-benign prostate hypertrophy agents, essential fatty acids, non-essential fatty acids, and mixtures thereof.

A wide variety of therapeutic agents can be used in conjunction with the present invention. The therapeutic agents (e.g. pharmaceutical agents) which may be used in the compositions of the present invention include both water soluble and water insoluble drugs. Examples of such therapeutic agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), naproxyn, diclofenac, indomethacin, flurbiprofen, ketoprofen, piroxican, sulindac, anti-emetics (e.g., metoclopramide), anti-epileptics (e.g., phenytoin, meprobamate and nitrazepam), vasodilators (e.g., nifedipine, papaverine, diltiazem and nicardipine), anti-tussive agents and expectorants (e.g., codeine phosphate), anti-asthmatics (e.g. theophylline and aminophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), anti-hypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

Examples of drugs whose efficacious amounts for use in the delivery system of the invention may be determined in this manner include anti-inflammatory agents, including non-steroidal and steroidal anti-inflammatory agents, such as indomethacin, diclofenac, flurbiprofen, aspirin, dexamethasone, budesonide, beclomethasone, flucticasone, tioxocortal, and hydrocortisone; immunosuppressants, such as cyclosporin; bronchodialators, such as salbutamol and theophylline; anti-anginals and anti-hypertensives, such as diltiazem, captopril, nifedipine, isosorbide dinitrate, oxyprenolol; anti-spasmodics, such as cimetropium bromide; anti-neoplastic agents, including methotrexate, tamoxifen, cyclophosphamide, mercaptopurine etoposide; anti-colitis drugs, such as 5-aminosalicylic; and anti-arrhythmia agents, such as quinidine, verapamil, procainamide and lidocaine; protein or peptide drugs, such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase; other hormones; vaccines; anti-coagulants, such as heparin or short chain heparin; and anti-migraine drugs, such as ergotamine.

Examples of agents that are useful for colonic delivery include nonsteroidal anti-inflammatory drugs (NSAID) such as diclofenac, flurbiprofen, indomethacin, and aspirin; steroid drugs such as dexamethasone, budesonide, beclomethasone, flucticasone, tioxocortol, and hydrocortisone; contraceptives or steroidal hormones such as estrogen, estradiol and testosterone; immunosuppressants such as cyclosporin; bronchodilators such as theophylline and salbutamol; anti-anginals and anti-hypertensives such as isosorbide dinitrate, isosorbide mononitrate, nitroglycerine, nifedipine, oxyprenolol, diltiazem, captopril, atenolol, benazepril, metoprolol, and vasopril; anti-spasmodic agents such as cimetropium bromide; anti-colitis agents such as 5-aminosalicylic acid; anti-arrhythmia agents such as quinidine, verapamil, procainamide, and lidocaine; anti-neoplastic agents such as methotrexate, tamoxifen, cyclophosphamide, mercaptopurine, and etoposide; protein or peptide drugs such as insulin, human growth hormone, interleukin-II, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase, other hormones and vaccines; anticoagulants such as heparin or short chain heparin; anti-migraine drugs such as ergotomine; glibenclamide; 5-hydroxytryptamine type$_{1A}$ receptor agonist gepiron; 511T3 antagonist ondansetron; metkephamid; menthol; antibiotics such as neomycin, beta-lactams such as ampicillin and amoxicillin, cephalosporins such as cephalexin and cloxacillin, and macrolides such as erythromycin; and PGE$_1$ analogues for protecting the gastroduodenal mucosa from NSATD injury, such as misoprostol. Protein drugs, such as LH-RH and insulin, may survive longer and be absorbed better from the colon than from the small intestine. Other drugs have been shown to possess colonic absorption, such as diclofenac, quinidine, theophylline, isosorbide dinitrate, nifedipine, oxprenolol, metoprolol, glibenclamide, 5-hydroxytryptamine type$_{1A}$ receptor agonist gepiron, 5HT3 antagonist ondansetron, metkephamid, menthol, benazepril (ACE inhibitor).

Examples of drugs that are useful for treating various other regions of the alimentary canal are as follows: Gastro Esophagal Reflux Disease—H2 receptor antagonists (e.g., Tagamet, Zantac), proton pump inhibitors (e.g., Omeprazole); Candida esophagitis—nystatin or clotrimazole; Duodenal Ulcer—H2 receptor agonists, prostaglandins (e.g., Cytotec, Prostin), proton pump inhibitors—(e.g., Prilosec, Omepra- zole, Sucralfate); Pathological Hypersecretory Conditions, Zollinger-Ellison Syndrome—H2 receptor agonists; Gastritis—H2 receptor agonists, PGE$_1$ analogs for protecting the gastroduodenal mucosa from NSAID injury such as misoprostol, GHR-IH drugs for treating pancreatitis, such as somatostatin, and anti-spasmodic drugs for treating local spasmolytic action such as cimetropium bromide.

The therapeutic benefits of the delivery system depend upon its ability to delivery efficacious levels of drugs to a specific site in the gastrointestinal tract. This allows the local treatment of diseases including, but not limited to, ulcerative colitis, Crohn's disease, colon carcinoma, esophagitis, Candida esophagitis, duodenal ulcers, gastric ulcers, Zollinger-Ellison Syndrome (gastrinoma), gastritis, chronic constipation, pancreatitis, local spasms, local infections, parasites, and other changes within the gastrointestinal tract due to effects of systemic disorders (e.g., vascular inflammatory, infectious and neoplastic conditions).

Active components may be added include, but are not limited to, a therapeutic substance or a pharmaceutically active agent such as a drug, a non-therapeutic substance such as a cosmetic substance, a local or general anesthetic or pain killer, or an opiate, a vaccine, an antigen, a microorganism, a sterilizing substance, a contraceptive composition, a protein or peptide such as insulin, an insecticide, a herbicide, a hormone such as a growth hormone or a seed germination hormone, a steroid, a toxin, or a marker substance. A non-limiting list of possible active components includes hydrochlorothiazide, acetazolamide, acetylsalicyclic acid, allopurinol, alprenolol, amiloride, antiarrhythmics, antibiotics, antidiabetics, antiepileptics, anticoagulants, antimycotics, atenolol, bendroflumethiazide, benzbromarone, benzthiazide, betamethasone, bronchodilators, buphenine, bupranolol, chemotherapeutics, chlordiazepoxide, chlorquine, chloro thiazide, chlorpromazine, chlortalidone, clenbuterol, clomipramine, clonidine, co-dergocrine, cortisone, dexamethasone, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxzolamide, fenoterol, fludrocortisone, fluphenazine, fluorosemide, gallopamil, guanethidine, hormones, hydrochlorothiazide, hydrocortisone, hydroflumethiazide, immunosuppresives, ibuprofen, imipramine, indomethacine, coronartherapeutics, levodopa, lithium salt, magnesium salt, medroxyprogesteron acetate, manadione, methaqualone, 8-methoxypsoralen, methylclothiazide, methyldopa, methylprednisolone, methyltestosterone, methylthiouracil, methylxanthine, metipranolol, molsidomine, morphine, naproxen, nicergline, nifedipine, norfenefrine, oxyphenbutazone, papaverine, parmathasone, pentobarbital, perphenazine, phenobarbital, phenylbutazone, phytomenadione, pirenzepine, polythiazide, prazosine, prednisolone, prednisone, probenecid, propranolol, propylthiouracil, rescinnamine, reserpine, secbutabarbital, secobarbital, spironolactone, sulfasalazine, sulfonamide, testosterone, thioridazine, triamcinolon, triamteren, trichloromethiazide, trifluoperazine, trifluopromazine, tuberculostatic, verapamil, virustatics, zytostatics, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen.

Suitable active ingredients are those which exert a local physiological effect, as well as those which exert a systemic effect, either following penetrating the mucosa or—in the case of oral administration—following transport to the gastro-intestinal tract with saliva. The bioadhesive dosage forms prepared from the compositions according to the present invention are particularly suitable for active ingredients which exert their activity during an extended period of time. Examples thereof are: analgesic and anti-inflammatory drugs (NSAIDs, acetyl salicylic acid, diclofenac sodium, ibuprofen, indomethacin, ketoprofen, meclofenamate sodium, mefenamic acid, naproxen sodium, paracetamol, piroxicam, tolmetin sodium); anti-arrhythmic drugs (procainamide HCl, quinidine sulphate, verapamil HCl); antibacterial agents (amoxicillin, ampicillin, benzathine penicillin, benzylpenicillin, cefaclor, cefadroxil, cephalexin, chloramphenicol, ciprofloxacin, clavulanic acid, clindamycin HCl, doxycycline HCl, erythromycin, flucloxacilline sodium, kanamycin sulphate, lincomycin HCl, minocycline HCl, nafcillin sodium, nalidixic acid, neomycin, norfloxacin, ofloxacin, oxacillin, phenoxymethyl-penicillin potassium); anti-coagulants (warfarin); antidepressants (amitriptyline HCl, amoxapine, butriptyline HCl, clomipramine HCl, desipramine HCl, dothiepin HCl, doxepin HCl, fluoxetine, gepirone, imipramine, lithium carbonate, mianserin HCl, milnacipran, nortriptyline HCl, paroxetine HCl); anti-diabetic drugs (glibenclamide); antifungal agents (amphotericin, clotrimazole, econazole, fluconazole, flucytosine, griseofulvin, itraconazole, ketoconazole, miconazole nitrate, nystatin); antihistamines (astemizole, cinnarizine, cyproheptadine HCl, flunarizine, oxatomide, promethazine, terfenadine); anti-hypertensive drugs (captopril, enalapril, ketanserin, lisinopril, minoxidil, prazosin HCl, ramipril, reserpine); anti-muscarinic agents (atropine sulphate, hyoscine); antivirals (acyclovir, AZT, ddC, ddI, ganciclovir, loviride, tivirapine, 3TC, delavirdine, indinavir, nelfinavir, ritonavir, saquinavir); sedating agents (alprazolam, buspirone HCl, chlordiazepoxide HCl, chlorpromazine, clozapine, diazepam, flupenthixol HCl, fluphenazine, flurazepam, lorazepam, mazapertine, olanzapine, oxazepam, pimozide, pipamperone, piracetam, promazine, risperidone, selfotel, seroquel, sulpiride, temazepam, thiothixene, triazolam, trifluperidol, ziprasidone); anti-stroke agents (lubeluzole, lubeluzole oxide, riluzole, aptiganel, eliprodil, remacemide); anti-migraine drugs (alniditan, sumatriptan); beta-adrenoceptor blocking agents (atenolol, carvedilol, metoprolol, nebivolol, propanolol); cardiac inotropic agents (digitoxin, digoxin, milrinone); corticosteroids (beclomethasone dipropionate, betamethasone, dexamethasone, hydrocortisone, methylprednisolone, prednisolone, prednisone, triamcinolone); disinfectants (chlorhexidine); diuretics (acetazolamide, frusemide, hydrochlorothiazide, isosorbide); anti-Parkinsonian drugs (bromocryptine mesylate, levodopa, selegiline HCl); enzymes; essential oils (anethole, anise oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme); gastro-intestinal agents (cimetidine, cisapride, clebopride, diphenoxylate HCl, domperidone, famotidine, lansoprazole, loperamide HCl, loperamide oxide, mesalazine, metoclopramide HCl mosapride, olsalazine, omeprazole, ranitidine, rabeprazole, ridogrel, sulphasalazine); haemostatics (aminocaproic acid); lipid regulating agents (lovastatin, pravastatin, probucol, simvastatin); local anaesthetics (benzocaine, lignocaine); opioid analgesics (buprenorphine HCl, codeine, dextromoramide, dihydrocodeine); parasympathomimetics (galanthamine, neostigmine, physostymine, tacrine, donepezil, ENA 713 (exelon), xanomeline); vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate).

Other active agents, which can be incorporated into the delivery system of the present invention, include therapeutic or prophylactic agents. These can be proteins or peptides, sugars, oligosaccharides, nucleic acid molecules, or other synthetic or natural agents. The agents may be labeled with a detectable label such as a fluorescent label or an enzymatic or chromatographically detectable agent.

Preferred drugs include antibiotics, antivirals, vaccines, vasodilators, vasoconstrictors, immunomodulatory compounds, including steroids, antihistamines, and cytokines such as interleukins, colony stimulating factors, tumor necrosis factor and interferon (alpha, beta, gamma), oligonucleotides including genes and antisense, nucleases, bronchodilators, hormones including reproductive hormones, calcitonin, insulin, erthropoietin, growth hormones, and other types of drugs such as Antiban™.

V. Diagnostic Applications and Gastrointestinal Imaging

The system of the present invention is also useful for diagnostic purposes, such as site-specific delivery of x-ray contrast agents, such as barium sulfate, siatrizoate sodium, iodine containing contrast agents, ultrasound contrast agents, contrast or enhancement agents for Magnetic Resonance Imaging, Tomography, or Positron Emission agents. The system is further useful for the delivery of monoclonal antibody markers for tumors.

The delivery system of the present invention can contain imaging agents that can be used in vascular imaging, as well as in applications to detect liver and renal diseases, in cardiology applications, in detecting and characterizing tumor masses and tissues, and in measuring peripheral blood velocity.

Barium sulfate suspension is the universal contrast medium used for examination of the upper gastrointestinal tract, as described by D. Sutton, Editor, A Textbook of Radiology and Imaging, Volume 2, Churchill Livingstone, London (1980), even though it has undesirable properties, such as unpalatability and a tendency to precipitate out of solution.

Several properties of the system are advantageous in diagnostic and gastrointestinal imaging, such as: (a) particle size: the rate of sedimentation is proportional to particle size (i.e., the finer the particle, the more stable the suspension); (b) non-ionic medium because charges on the barium sulfate particles influence the rate of aggregation of the particles, and aggregation is enhanced in the presence of the gastric contents; and (c) solution pH: suspension stability is best at pH 5.3, however, as the suspension passes through the stomach, it is inevitably acidified and tends to precipitate.

The encapsulation of barium sulfate in the matrix composition and articles found of the matrix composition can help in coating, preferentially, the gastric mucosa in the presence of excessive gastric fluid. With bioadhesiveness targeted to more distal segments of the gastrointestinal tract, it can also provide a kind of wall imaging not easily obtained otherwise.

The double contrast technique, which utilizes both gas and barium sulfate to enhance the imaging process, uses a proper coating of the mucosal surface. To achieve a double contrast, air or carbon dioxide must be introduced into the patient's gastrointestinal tract. This is typically achieved via a naso-gastric tube to provoke a controlled degree of gastric distension. Comparable results can be obtained by the release of individual gas bubbles in a large number of individual adhesive microspheres of the present invention and this imaging process can apply to intestinal segments beyond the stomach.

An in vivo method for evaluating bioadhesion uses encapsulation of a radio-opaque material, such as barium sulfate, or both a radio-opaque material and a gas-evolving agent, such as sodium carbonate, within a bioadhesive polymer. After oral administration of this radio-opaque material, its distribution in the gastric and intestinal areas is examined using image analysis.

Controlled-release dosage form of azithromycin which limits the release rate of azithromycin in the G-I tract, i.e., sustains the release of azithromycin at the pH of the stomach and releases azithromycin at the pH of the small intestine and colon, results with dosage forms that have reduced side effect. A pH dependent anionic polymer solubilizing above pH 7.0 can be used in the delivery system of the present invention for starting the delivery of the drug in the small intestine and colon. The object of encapsulating this drug in the controlled release system of the present invention is to decrease the incidence and severity of azithromycin-induced G-I side effects. This is particularly useful at high doses, for example 2 g and up, at which the incidence of gastrointestinal side effects can be relatively high. Minimizing exposure of the duodenum to azithromycin reduces the overall incidence and severity of azithromycin-induced gastrointestinal side effects. The controlled release system of the present invention can be incorporated in dosage forms and deliver therapeutically useful doses of azithromycin, while reducing localized exposure of azithromycin throughout the G-I tract, especially at the duodenum, thereby decreasing gastrointestinal side effects.

In one embodiment, the controlled release delivery system of the present invention comprises about 1% to about 50% hydrophobic material, about 1% to about 50% pH sensitive material, about 0% to about 50% water sensitive material and about 0% to about 30% azithromycin.

An active ingredient, drug, which can be encapsulated in the nanospheres of the present invention is pseudoephedrine, an adrenergic (vasoconstrictor) agent with the chemical name [S—(R*,R*)]-a-[1-(methylamino)ethyl]-benzenemethanol HCl for treating microbial infections. Pseudoephedrine is used to relieve nasal or sinus congestion (stuffiness) caused by the common cold, sinusitis, and hay fever and other respiratory allergies. It is also used to relieve ear congestion caused by ear inflammation or infection. It is commonly added to codeine in 'cold & flu' products. The effects of Pseudoephedrine are similar to epinephrine, and central effects are similar to, but less intense than, amphetamines. The molecular formula is $C_{10}H_{15}NO.HCl$. Pseudoephedrine HCl occurs as fine, white to off-white crystals or powder, having a faint characteristic odor.

Controlled-release dosage form of Pseudoephedrine which limits the release rate of Pseudoephedrine in the G-I tract, i.e., sustains the release of Pseudoephedrine at the pH of the stomach and releases pseudoephedrine at the pH of the small intestine and colon, results with dosage forms that have reduced side effect. A pH dependent anionic polymer solubilizing above pH 7.0 is utilized for starting the delivery of the drug in the small intestine and colon. The object of encapsulating this drug in the controlled release system of the present invention is to decrease the incidence and severity of Pseudoephedrine-induced G-I side effects. The controlled release system of the present invention can be incorporated in dosage forms and deliver therapeutically useful doses of Pseudoephedrine, while reducing localized exposure of Pseudoephedrine throughout the G-I tract, especially at the duodenum, thereby decreasing gastrointestinal side effects.

V. Processing Method

Va. Nano-Spheres

The encapsulated active agent in the nano-spheres of the present invention can be prepared by the steps of (1) heating a hydrophobic materials to a temperature above the melting point to form a melt, (2) dissolving or dispersing the active agent in the melt, (3) emulsifying the melt in the aqueous phase; and (4) cooling the dispersion to ambient temperature to form a fine suspension.

The active ingredients can be incorporated into hydrophobic solid nano-spheres, the pH sensitive micro-sphere, or in both the nano and micro spheres.

Vb. Micro-Spheres

The controlled release system of the present invention can be prepared by the steps of (a) incorporating the selected active agents into the hydrophobic interior of the nano-spheres, (b) forming an aqueous mixture comprising one or more active agents, the nano-spheres, and a pH sensitive material, and (c) spray drying the mixture of the present invention to form a dry powder composition. Accordingly, the nano-spheres can be encapsulated into the micro-sphere structure. One or more of the active agents which can be the same or different than the active agents incorporated in the nano-sphere can be incorporated into the micro-sphere structure.

A process for producing the multi component controlled release system includes the following steps:

(i) heating a hydrophobic material to a temperature above the melting point to form a melt;

(ii) dissolving or dispersing the selected first active agent into the melt;

(iii) dissolving or dispersing a second active agent, and the pH sensitive materials, in the aqueous phase and heating it to above the melting temperature of the hydrophobic material;

(iv) mixing the hot melt with the aqueous phase to form a dispersion;

(v) high shear homogenization of the dispersion at a temperature above the melting temperature until a homogeneous fine dispersion is obtained having a sphere size of from about 1 microns to about 2 microns;

(vi) cooling the dispersion to ambient temperature; and (vii) spray drying the emulsified mixed suspension to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245-265; Barreto, "Spray Dried Perfumes for Specialties, Soap and Chemical Specialties", December 1966; Maleeny, Spray Dried Perfumes, Soap and San Chem, January 1958, pp. 135 et seq.; Flinn and Nack, "Advances in Microencapsulation Techniques", Batelle Technical Review, Vo. 16, No. 2, pp. 2-8 (1967); U.S. Pat. Nos. 5,525,367; and 5,417,153 which are incorporated herein as references.

The use of pH activated micro-spheres which provide varying rates of diffusion are contemplated. For example, the active ingredients encapsulated in the pH activated microspheres may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

Nano-spheres formed of a hydrophobic material provide a controlled release system in order to release the active agent over an extended period of time by molecular diffusion. Active agents in the hydrophobic matrix of the nano-spheres can be released by transient diffusion. The theoretical early and late time approximation of the release rate of the active ingredients dissolved in the hydrophobic matrix of the nano-spheres can be calculated from the following equations:

Early Time Approximation $$(m_t/m_{sec}) < 0.4$$

$$\frac{M_t}{M_\infty} = 4\left(\frac{D_p t}{\Pi r^2}\right)^{1/2} - \frac{D_p t}{r^2} \quad (1)$$

$$\frac{dM_t/M_\infty}{dt} = 2\left(\frac{D_p}{\Pi r^2 t}\right)^{1/2} - \frac{D_p}{r^2} \quad (2)$$

Late Time Approximation $$(m_t/m_\infty) > 0.6$$

$$\frac{M_t}{M_\infty} = 1 - \frac{4}{(2.405)^2}\exp\left(\frac{-(2.405)^2 D_p t}{r^2}\right) \quad (3)$$

$$\frac{dM_t/M_\infty}{dt} = 1 - \frac{4D_p}{r^2}\exp\left(\frac{-(2.405)^2 D_p t}{r^2}\right) \quad (4)$$

wherein:

r is the radius of the sphere, $m_\infty$ is the amount of active agent released from the controlled release system after infinite time;

$m_t$ is the amount of active agent released from the controlled release system after time t; and $D_p$ is the diffusion coefficient of the active agent in the matrix.

The release rate for releasing the active agents from the hydrophobic nano-spheres is typically slower than the release rate for releasing active agent from the pH sensitive matrix. The active agents can be selected to be incorporated into either the hydrophobic nano-spheres or the pH sensitive matrix depending on the desired time for release of the active agents. For example, a predetermined first active agent can be incorporated in the pH or salt sensitive matrix to be released during the rinsing cycle and a predetermined second active agent can be incorporated in the hydrophobic nano-spheres for release over an extended period of time during release of the first agent or after the first agent has been released. For example, the pH sensitive matrix formed in accordance with the present invention can release the first active agent at a predetermined pH or salt concentration to provide a "burst" with continued release of the first active agent and nano-spheres formed in accordance with the present invention can release the active agent depending on the release rate from an initial time such as a day or within few days, up to a period of few weeks.

In the preferred embodiment, the active agent is present at a level from about 0.01% to about 60%, preferably from about 1% to about 50% by weight of the micro-sphere. In the preferred embodiment, the nano-spheres are generally present in the pH sensitive matrix at a level from about 1% to about 80%, preferably from about 1% to about 60% by weight of the matrix material with the balance being the active agents, and the pH sensitive materials. In the preferred embodiment, the pH sensitive matrix is generally present at a level from about 1% to about 80%, preferably from about 1% to about 60% by weight of the matrix material with the balance being the active agents, and the hydrophobic materials.

The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20-100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient.

Pharmaceutical compositions thus comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The carrier system of the present invention can be incorporated in pharmaceutical and health care products.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Preparation of a pH Sensitive Drug Delivery System

Example 1

The following procedure is used for the preparation of multi component controlled release system with a drug as the active agent in the hydrophobic nano-sphere matrix. The nano-sphere hydrophobic matrix is candelilla wax, commercially available from Strahl & Pitsch Inc. of West Babylon, N.Y. The micro-sphere pH sensitive matrix is EUDRAGIT® S 100 pH dependent anionic polymer solubilizing above pH 7.0 for delivery of the drug in the small intestine and colon (commercially available from Rohm America Inc. of Piscataway, N.J.) for releasing the nano-spheres in the duodenum, the water sensitive matrix is Hi-Cap™ 100 (commercially available from the National Starch and Chemical Company of Bridgewater, N.J.).

400 grams of candelilla wax is placed in an oven at 80 degrees ° C. and allowed to melt. 1500 grams of deionized water are placed into 1 gallon vessel, fitted with an all-purpose silicon rubber heater (Cole-Palmer Instrument Company). 400 grams of Eudragit® S 100 (commercially available from Rohm America Inc. of Piscataway, N.J.) and 100 grams of Hi-Cap™ 100 (commercially available from the National Starch and Chemical Company of Bridgewater, N.J.) were added to the water and the aqueous solution is heated to 90 degree C. while mixing it with a propeller mixer. The candelilla wax is removed from the oven. 100 grams of azithromycin are mixed into the melt by hand with a glass rod. The drug/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 25% azithromycin encapsulated in the solid hydrophobic nano-spheres. The multi component controlled release system obtained contains 10% azithromycin, 40% candelilla wax, 40% pH sensitive material, and 10% water sensitive material.

Example 2

The following procedure is used for the preparation of multi component controlled release system with a drug as the active agent in the hydrophobic nano-sphere matrix. The nano-sphere hydrophobic matrix is candelilla wax, commercially available from Strahl & Pitsch Inc. of West Babylon, N.Y. The micro-sphere pH sensitive matrix is EUDRAGIT® S 100 pH dependent anionic polymer solubilizing above pH 7.0 for delivery of the drug in the small intestine and colon (commercially available from Rohm America Inc. of Piscataway, N.J.) for releasing the nano-spheres in the duodenum, the water sensitive matrix is Hi-Cap™ 100 (commercially available from the National Starch and Chemical Company of Bridgewater, N.J.).

400 grams of beeswax wax is placed in an oven at 80 degrees ° C. and allowed to melt. 1500 grams of deionized water are placed into 1 gallon vessel, fitted with an all-purpose silicon rubber heater (Cole-Palmer Instrument Company). 400 grams of Eudragit® S 100 (commercially available from Rohm America Inc. of Piscataway, N.J.) and 100 grams of Hi-Cap™ 100 (commercially available from the National Starch and Chemical Company of Bridgewater, N.J.) were added to the water and the aqueous solution is heated to 90 degree C. while mixing it with a propeller mixer. The beeswax is removed from the oven, 100 grams of Pseudoephedrine are mixed into the melt by hand with a glass rod. The drug/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 25% Pseudoephedrine encapsulated in the solid hydrophobic nano-spheres. The multi component controlled release system obtained contains 10% Pseudoephedrine, 40% beeswax, 40% pH sensitive material, and 10% water sensitive material.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A multi-component controlled release composition comprising:

a plurality of solid nano-spheres encapsulated in a pH-sensitive or salt-sensitive micro-sphere, said pH-sensitive or salt-sensitive micro-sphere being formed of a pH-sensitive or salt-sensitive matrix material, and a first pharmaceutical active agent incorporated by dispersion into a hydrophobic matrix forming the core of said plurality of solid nano-spheres or incorporated into both said hydrophobic matrix of said plurality of solid nano-spheres by dispersion and said matrix material of said micro-sphere, wherein said nano-spheres contact said matrix material of said microsphere, wherein said solid nano-spheres are formed of a wax material that has a melting point in the range of between about 25 degrees C. and about 150 degrees C. wherein said first pharmaceutical active agent is incorporated in said hydrophobic matrix of said solid nano-spheres and further comprising a second pharmaceutical active agent homogeneously incorporated in said pH-sensitive or salt-sensitive matrix material of said microsphere wherein said pH-sensitive or salt-sensitive matrix material of said microsphere releases said second active agent upon contact with a solution having a predetermined pH or predetermined salt concentration, wherein said first pharmaceutical active agent and said second pharmaceutical active agent are not the same, wherein said first pharmaceutical active is released continuously thereafter for an extended period of time, and wherein said micro-sphere has a size of from about 20 to about 100 microns and each of said nano-spheres has an average size of about 0.01 to about 5 microns.

2. The composition according to claim 1 wherein said pH-sensitive micro-sphere degrades or dissolves when said pH-sensitive micro-sphere contacts a solution having a pH in the range of about 3 to about 12.

3. The composition according to claim 1 wherein said pH-sensitive or salt-sensitive matrix material degrades or dissolves when said pH-sensitive micro-sphere contacts a solution having a pH greater than about 5.

4. The composition according to claim 1 wherein said pH-sensitive or salt-sensitive matrix material is a cationic pH-sensitive polymer that is water insoluble at a pH above about 9 and is water soluble at a pH of about 7 or below.

5. The composition of claim 1 wherein said pH-sensitive material is selected from the group consisting of:
acrylate polymers with amino substituents, acrylic acid esters, polyacrylamides, phthalate derivatives and mixtures thereof.

6. The composition of claim 1 wherein said pH-sensitive material is selected from the group consisting of:
acid phthalate of carbohydrate, amylose acetate phthalate, cellulose acetate phthalate, cellulose ester phthalate, cellulose ether phthalate, hydroxy propyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymer, gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivative, acrylic acid and acrylic ester copolymers, methacrylic acid, methacrylic acid ester, vinyl acetate, crotonic acid copolymer and mixtures thereof.

7. The composition according to claim 1 wherein a first portion of said plurality of nano-spheres are adhered to a second portion of said plurality of nano-spheres with a pH-sensitive or salt-sensitive matrix material.

8. The composition according to claim 1 further comprising a moisture sensitive material mixed with said pH-sensitive or salt-sensitive material of said micro-sphere.

9. The composition according to claim 8 wherein said moisture sensitive material is selected from the group consisting of polyvinyl pyrrolidone, water soluble cellulose, polyvinyl alcohol, ethylene maleic anhydride copolymer, methyl vinyl ether maleic anhydride copolymer, polyethylene oxides, polyamide, polyester, copolymers or homopolymers of acrylic acid, polyacrylic acid, polystyrene acrylic acid copolymer, starch derivatives, polyvinyl alcohol, acrylic acid copolymer, anionic polymer of methacrylic acid and methacrylate, cationic polymer having dimethyl-aminoethyl ammonium functional groups, hydroxyethyl cellulose, carboxymethyl cellulose, hydroxymethyl cellulose, carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, polysaccharide, hydrocolloid, natural gum, protein, and mixtures thereof.

10. The composition of claim 1 wherein said pH-sensitive material is relatively insoluble and impermeable at the pH of the stomach and is more soluble and permeable at the pH of the small intestine and colon.

11. The composition of claim 10 wherein said pH-sensitive material is selected from the group consisting of polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers.

12. The composition of claim 1 wherein said wax material has a penetration point of about 1 to about 10.

13. The composition of claim 1 wherein said wax material is selected from the group consisting of:
natural wax, synthetic wax, regenerated wax, vegetable wax, animal wax, mineral wax, petroleum wax, microcrystalline wax and mixtures thereof.

14. The composition of claim 1 wherein said wax comprises one or more of carnauba wax, candelilla wax and beeswax.

15. The composition of claim 1, wherein said micro-sphere further comprises a water sensitive material selected from the group consisting of:
natural oligomer, synthetic oligomer, natural polymer, synthetic polymer and copolymer, starch, starch derivative, oligosaccharide, polysaccharide, hydrocolloid, natural gum, protein, cellulose, cellulose derivative and mixtures thereof.

16. The composition of claim 1 further comprising a bioadhesive material incorporated into said solid nano-sphere or said micro-sphere or in both said nano-sphere and said micro-sphere.

17. The composition of claim 16 wherein said bioadhesive material is a bioadhesive polymer.

18. The composition of claim 17 wherein said bioadhesive polymer is selected from the group consisting of polyhyaluronic acids, casein, gelatin, glutin, polyanhydrides, polyacrylic acid, alginate, chitosan, poly(methyl methacrylates), poly(ethyl methacrylates), poly (butyl methacrylate), poly (isobutyl methacrylate), poly(hexylmethacrylate), poly(isodecylmethacrylate), poly(lauryl methacrylate), polyphenyl methacrylate), poly(methyl acrylate), poly(isopropyl acrylate), poly(isobutyl acrylate), poly(octadecyl acrylate) and poly(fumaric-co-sebacic)acid.

19. The composition of claim 1 wherein said nano-sphere further comprises a ligand.

20. The composition of claim 1 wherein said nano-sphere comprises a targeting material selected from the group comprising lectin, viral protein, bacterial protein, monoclonal antibody and antibody fragment.

21. The composition of claim 1 wherein said first pharmaceutical active agent is selected from the group consisting of:
analgesic, antihistamine, anti-emetic, anti-epileptic, vasodilator, anti-tussive agent, expectorant, anti-hypotensive, anti-inflammatory agent, anthelmintic, anti-arrhythmic agent, anti-bacterial agent, anti-viral agent, anti-coagulant, anti-depressant, anti-diabetic, anti-epileptic, anti-fungal agent, anti-gout agent, anti-hypertensive agent, anti-malarial, anti-migraine agent, anti-muscarinic agent, anti-neoplastic agent, anti-stroke agent, erectile dysfunction improvement agent, immunosuppressant, anti-protozoal agent, anti-thyroid agent, anxiolytic agent, sedative, hypnotic, neuroleptic, beta-Blocker, cardiac inotropic agent, corticosteroid, diuretic, anti-parkinsonian agent, gastro-intestinal agent, histamine receptor antagonist, keratolytic, lipid regulating agent, anti-anginal agent, cox-2-inhibitor, leukotriene inhibitor, macrolide, muscle relaxant, nutritional agent, opioid analgesic, protease inhibitor, sex hormone, muscle relaxant, anti-osteoporosis agent, anti-obesity agent, cognition enhancer, anti-urinary incontinence agent, nutritional oil, anti-benign prostate hypertrophy agent, essential fatty acid, non-essential fatty acid, antihemorrhoidal, psychotropic, antidiarrheal, mucolytic, decongestant, laxative, vitamin, stimulant, appetite suppressant, contraceptive, protein, peptide, sugar, natural agent and mixtures thereof.

22. The composition of claim 1 wherein said first pharmaceutical active agent is one or more of a drug or steroid.

23. The composition of claim 22 wherein said drug is selected from the group consisting of:
antibiotic, antiviral, antigen, vaccine, vasodilator, vasoconstrictor, immunomodulatory compound, cytokine, colony stimulating factor, tumor necrosis factor, interferon, oligonucleotide, nuclease, bronchodilator, hormone, calcitonin, insulin, erthropoietin, growth hormone and mixtures thereof.

24. The composition of claim 1 wherein said first pharmaceutical active agent is delivered to the colon.

25. The composition of claim 24 wherein said first pharmaceutical active agent is selected from the group consisting of:
nonsteroidal anti-inflammatory drug (NSAID), steroid drug, contraceptive, steroidal hormone, immunosuppressant, bronchodilator, anti-anginal, anti-hypertensive, anti-spasmodic agent, anti-colitis agent, anti-arrhythmia agent, anti-neoplastic agent, protein drug, peptide drug, interferon, calcitonin, leuprolide, tumor necrosis factor, bone growth factor, melanocyte-stimulating hormone, captopril, somatostatin, somatostatin octapeptide analog, cyclosporin, renin inhibitor, superoxide dismutase, vaccine, anticoagulant, anti-migraine drug, 5-hydroxytryptamine antagonistondansetron, menthol, antibiotic, beta-lactam, cephalosporin, macrolide, analogues for protecting the gastroduodenal mucosa from NSAID injury, and mixtures thereof.

26. The composition of claim 1 wherein said first pharmaceutical active agent is delivered to an alimentary canal.

27. The composition of claim 1 wherein said first pharmaceutical active agent is delivered to the stomach and/or small intestine.

28. The composition of claim 1 wherein said first pharmaceutical active agent is delivered to the gastrointestinal tract.

29. The composition of claim 1 wherein said first pharmaceutical active agent is an imaging agent.

30. The composition of claim 29 wherein said imaging agent is one or more of barium sulfate, siatrizoate sodium iodine containing contrast agents, ultra sound contrast agents, magnetic resonance imaging contrast agents, magnetic resonance imaging enhancements, tomography agents, and positron emission agents.

31. The composition of claim 1 wherein said pharmaceutical active agent is azithromycin and said pH-sensitive or salt-sensitive matrix composition is a pH dependent anionic polymer soluble at a pH above about 7.0 for delivering an azithromycin to the small intestine or colon.

32. The composition of claim 1 wherein said pharmaceutical active agent is pseudoephedrine and said pH-sensitive or salt-sensitive matrix composition is a pH dependent anionic polymer soluble at a pH above about 7.0 for delivering pseudoephedrine to the small intestine or colon.

33. The composition of claim 1 wherein said nano-spheres further comprise a cationic surface active agent, anionic surface active agent, a nonionic surface active agent or a zwitterionic surface active agent.

34. The composition according to claim 1 wherein the extended period of time is in the range of a day to a period of a few weeks.

35. The composition according to claim 1 wherein the makeup of said microsphere and said plurality of nano-spheres functions to provide that upon contact with said solution, said second pharmaceutical agent releases in a burst and said first pharmaceutical agent releases continuously thereafter for the extended period of time.

36. The composition according to claim 35 wherein the extended period of time is in the range of a day to a period of a few weeks.

37. A pharmaceutical composition comprising a pharmaceutically and physiologically suitable carrier and a controlled release composition, the controlled release composition comprising:
a plurality of solid nano-spheres encapsulated in a pH-sensitive or salt-sensitive micro-sphere, said pH-sensitive or salt-sensitive micro-sphere being formed of a pH-sensitive or salt-sensitive matrix material, wherein said micro-sphere has a size of from about 20 to about 100 microns and each of said nano-spheres has an average size of about 0.01 to about 5 microns, wherein said solid nano-spheres are formed of a wax material that has a melting point in the range of between about 25 degrees C. and about 150 degrees C. and
a first pharmaceutical active agent incorporated into said plurality of solid nano-spheres or into both said micro-sphere or said nano-sphere, wherein said active agent is dispersed throughout a hydrophobic matrix of said solid nano-sphere or said matrix material of said micro sphere in a quantity sufficient for administration in a single or multiple dose regimen to a mammal, and wherein the hydrophobic nano-spheres contact said matrix material of said microsphere.

38. The pharmaceutical composition according to claim 37 formulated into a dosage form for administration, in which said dosage form is selected from the group consisting of powder, tablets, capsules and injectable compositions.

39. An article formed of the composition of claim 1.

40. A method for delivering an active substance to a preselected environment; said method comprising introducing to said environment a controlled release composition comprising: a plurality of solid nano-spheres, said plurality of solid nano-spheres being encapsulated in a pH-sensitive or salt-sensitive microsphere, wherein said solid nano-spheres are formed of a wax material that has a melting point in the range of between about 25 degrees C. and about 150 degrees C. said pH-sensitive or salt-sensitive microsphere being formed of a pH-sensitive or salt-sensitive matrix material, and a first pharmaceutical active agent incorporated into a hydrophobic matrix of said plurality of solid nano-spheres or said microsphere or in both said hydrophobic matrix of said plurality of solid nano-spheres and said micro-sphere, wherein said active agent is dispersed throughout said solid nano-sphere or said matrix material of said microsphere, wherein said hydrophobic nano-spheres contact said pH-sensitive or salt-sensitive matrix material of said microsphere;
wherein said micro-sphere has a size of from about 20 to about 100 microns and each of said nano-spheres has an average size of about 0.01 to about 5 microns, and
wherein introducing said composition into said environment permits degradation of said composition and release of said active agent.

41. The method of claim 40 wherein said environment is the stomach or small intestine.

42. The method of claim 40 wherein said pH-sensitive micro-sphere degrades or dissolves when said pH-sensitive microsphere contacts a solution having a pH in the range of about 3 to about 12.

43. The method of claim 40 wherein said pH-sensitive material is selected from the group consisting of:
acid phthalate of carbohydrate, amylose acetate phthalate, cellulose acetate phthalate, cellulose ester phthalate, cellulose ether phthalate, hydroxy propyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymer, gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivative, acrylic acid and acrylic ester copolymers, methacrylic acid, methacrylic acid ester, vinyl acetate, crotonic acid copolymer and mixtures thereof.

44. The method of claim 40 wherein a first portion of said plurality of nano-spheres is adhered to a second portion of said plurality of nano-spheres by means of a pH-sensitive or salt-sensitive matrix material.

45. The method of claim 40 thither comprising a moisture sensitive material mixed with said pH-sensitive or salt-sensitive material of said micro-sphere.

46. The method of claim 40 wherein said active agent is selected from the group consisting of:
analgesic, antihistamine, anti-emetic, anti-epileptic, vasodilator, anti-tussive agent, expectorant, anti-hypotensive, anti-inflammatory agent, anthelmintic, anti-arrhythmic agent, anti-bacterial agent, anti-viral agent, anti-coagulant, anti-depressant, anti-diabetic, anti-epileptic, anti-fungal agent, anti-gout agent, anti-hypertensive agent, anti-malarial, anti-migraine agent, anti-muscarinic agent, anti-neoplastic agent, anti-stroke agent, erectile dysfunction improvement agent, immunosuppressant, anti-protozoal agent, anti-thyroid agent, anxiolytic agent, sedative, hypnotic, neuroleptic, beta-Blocker, cardiac inotropic agent, corticosteroid, diuretic, anti-parkinsonian agent, gastro-intestinal agent, histamine receptor antagonist, keratolytic, lipid regulating agent, anti-anginal agent, cox-2-inhibitor, leukotriene inhibitor, macrolide, muscle relaxant, nutritional agent, opioid analgesic, protease inhibitor, sex hormone, muscle relaxant, anti-osteoporosis agent, anti-obesity agent, cognition enhancer, anti-urinary incontinence agent, nutritional oil, anti-benign prostate hypertrophy agent, essential fatty acid, non-essential fatty acid, antihemorrhoidal, psychotropic, antidiarrheal, mucolytic, decongestant, laxative, vitamin, stimulant, appetite suppressant, contraceptive, protein, peptide, sugar, natural agent and mixtures thereof.

47. The method of claim 40 wherein said first pharmaceutical active agent is one or more of a pharmaceutical agent, cosmetic substance, drug or steroid.

48. The method of claim 40 wherein said active agent is selected from the group consisting of:
antibiotic, antiviral, antigen, vaccine, vasodilator, vasoconstrictor, immunomodulatory compound, cytokine, colony stimulating factor, tumor necrosis factor, interferon, oligonucleotide, nuclease, bronchodilator, hormone, calcitonin, insulin, erthropoietin, growth hormone and mixtures thereof.

49. The method of claim 40 wherein said environment is the colon.

50. The method of claim 40 wherein said environment is an alimentary canal.

51. The method of claim 40 wherein said environment is the gastrointestinal tract.

52. The method of claim 40 wherein said active agent is an imaging agent.

53. The method of claim 52, wherein said imaging agent is one or more of barium sulfate, siatrizoate sodium and iodine containing contrast agents.

54. The method of claim 40 further comprising a bioadhesive material incorporated into said plurality of solid nano-spheres or said micro-sphere or into both said plurality of solid nano-spheres and said micro-sphere.

55. The method of claim 40 wherein said bioadhesive material is a bioadhesive polymer.

56. The method of claim 40 wherein said nano-sphere further comprises a ligand.

57. The method of claim 40 wherein said nano-sphere comprises a targeting material selected from the group comprising lectin, viral protein, bacterial protein, monoclonal antibody and antibody fragment.

58. A controlled release composition comprising:
a first active agent;
a plurality of solid nano-spheres formed of a hydrophobic matrix at its core; wherein said solid nano-spheres are formed of a wax material that has a melting point in the range of between about 25 degrees C. and about 150 degrees C. and
a micro-sphere formed of a pH-sensitive or salt-sensitive matrix;
wherein said first active agent is incorporated by dispersion in and dispersed throughout said hydrophobic matrix of said nano-spheres and said pH-sensitive or salt-sensitive matrix of said microsphere, wherein said first pharmaceutical active agent is incorporated in said hydrophobic matrix of said solid nano-spheres and further comprising a second pharmaceutical active agent homogeneously incorporated in said pH-sensitive or salt-sensitive matrix material of said micro sphere wherein said pH-sensitive or salt-sensitive matrix material of said microsphere releases said second active agent upon contact with a solution having a predetermined pH or predetermined salt concentration,
wherein said first pharmaceutical active agent and said second pharmaceutical active agent are not the same, and,
wherein said microsphere has a size of from about 20 to about 100 microns and each of said nano-spheres has an average size of about 0.01 to about 5 microns.

* * * * *

Disclaimer

7,670,627 B2 — Adi Shefer, Dayton, NJ (US); and Samuel David Shefer, Dayton, NJ (US). PH TRIGGERED TARGETED CONTROLLED RELEASE SYSTEMS FOR THE DELIVERY OF PHARMACEUTICAL ACTIVE INGREDIENTS. Patent dated Mar. 2, 2010. Disclaimer filed September 20, 2012, by the assignee, Salvona LLC.

The term of this patent shall not extend beyond the expiration date of patent no. 7,053,034.

*(Official Gazette, November 12, 2013)*